US009451976B2

(12) United States Patent
Schneider et al.

(10) Patent No.: US 9,451,976 B2
(45) Date of Patent: Sep. 27, 2016

(54) MEDICAL HANDLE

(75) Inventors: Rainer Schneider, St. Pantaleon (AT); Rainer Schroeck, Lamprechtshausen (AT); Walter Pletscher, Oberzeiring (AT); Josef Ott, Zeltweg (AT)

(73) Assignee: Arthrex, Inc., Naples, FL (US)

( * ) Notice: Subject to any disclaimer, the term of this patent is extended or adjusted under 35 U.S.C. 154(b) by 1819 days.

(21) Appl. No.: 12/009,619

(22) Filed: Jan. 17, 2008

(65) Prior Publication Data
US 2008/0170841 A1 Jul. 17, 2008

(30) Foreign Application Priority Data

Jan. 17, 2007 (EP) .................................. 07000834

(51) Int. Cl.
*A61B 17/30* (2006.01)
*A61B 17/32* (2006.01)
*H02K 29/08* (2006.01)
*H02P 5/00* (2016.01)
*H02K 7/14* (2006.01)

(52) U.S. Cl.
CPC ....... *A61B 17/32002* (2013.01); *H02K 11/215* (2016.01); *H02K 29/08* (2013.01); *A61B 2017/320028* (2013.01); *A61B 2090/0813* (2016.02); *H02K 7/145* (2013.01)

(58) Field of Classification Search
CPC .. H02K 11/0021; H02K 29/08; H02K 7/145; A61B 17/32002; A61B 2007/320028; A61B 2009/4868
USPC .................... 388/800, 907, 937, 931; 606/1; 318/114, 119, 139, 280
See application file for complete search history.

(56) References Cited

U.S. PATENT DOCUMENTS

| 4,998,865 | A | * | 3/1991 | Nakanishi et al. ........ 417/423.7 |
| 5,270,622 | A | | 12/1993 | Krause |
| 5,747,953 | A | * | 5/1998 | Philipp .......................... 318/139 |
| 5,998,892 | A | * | 12/1999 | Smith et al. ................ 310/68 B |
| 6,013,991 | A | | 1/2000 | Philipp |

(Continued)

FOREIGN PATENT DOCUMENTS

WO 2007/000218 1/2007

OTHER PUBLICATIONS

International Search Report for EP 07 00 0834 (Mailed Jun. 21, 2007).

Primary Examiner — Gary Jackson
Assistant Examiner — Boniface N Nganga
(74) Attorney, Agent, or Firm — Blank Rome LLP

(57) ABSTRACT

A medical handle comprises a drive unit and a control device or circuit for driving a medical tool. The control device or circuit comprises a control and/or regulating circuit for controlling and/or regulating the drive unit, the drive unit comprises at least one magnetic element and a sensor system for determining the alignment of the at least one magnetic element. To achieve simpler assembly and a greater resistance to the ambient conditions that prevail during sterilization in comparison with known handles, the sensor system and the control and/or regulating circuit are combined in a joint control module, and the at least one magnetic element is arranged in the medical handle in such a way that at least a part of the control module can be positioned in the immediate vicinity of the at least one magnetic element and that the sensor system is arranged in the control module in such a way that it can be positioned in the immediate vicinity of the at least one magnetic element.

20 Claims, 2 Drawing Sheets

(56) References Cited

U.S. PATENT DOCUMENTS

| | | | |
|---|---|---|---|
| 6,071,093 A * | 6/2000 | Hart | 417/424.2 |
| 6,707,188 B2 * | 3/2004 | Torii et al. | 310/75 R |
| 7,057,317 B2 * | 6/2006 | Kuwert | 310/89 |
| 2001/0033742 A1 * | 10/2001 | Weaver et al. | 388/800 |
| 2001/0043806 A1 | 11/2001 | Gorti et al. | |
| 2003/0173925 A1 * | 9/2003 | Strobl et al. | 318/543 |
| 2004/0183386 A1 * | 9/2004 | Kuwert | 310/89 |
| 2005/0107814 A1 | 5/2005 | Johnston et al. | |
| 2005/0162028 A1 * | 7/2005 | Kardeis et al. | 310/156.06 |
| 2005/0206254 A1 * | 9/2005 | Tsuge et al. | 310/68 B |
| 2006/0108881 A1 * | 5/2006 | Hauger et al. | 310/68 B |
| 2006/0125334 A1 * | 6/2006 | Kataoka et al. | 310/68 B |
| 2007/0085496 A1 * | 4/2007 | Philipp et al. | 318/139 |
| 2008/0174213 A1 * | 7/2008 | Peterson et al. | 310/68 R |

* cited by examiner

MEDICAL HANDLE

CROSS REFERENCE TO RELATED APPLICATION

The present application claims priority from pending European Patent Application No. 07000834.7, filed Jan. 17, 2007, which is incorporated herein by reference.

BACKGROUND

1. Field

The present application relates to a medical handle having a drive unit for driving a medical tool and a control and/or regulating circuit for controlling and/or regulating the drive unit.

2. Description of Prior Art

Such handles are widely used today for a number of different medical, surgical and cosmetic procedures. The drive unit of these handles often comprises a brushless electric motor which generates a rotational movement that is transferred to a treatment tool. The drive unit may optionally have one or more shafts for transferring the rotational movement, gears or devices for converting the rotational movement into a different type of motion.

Brushless electric motors for the handles are usually controllable and in most cases the user can at least vary the rotational speed of the motor via a control element and a control device. The basic design of such a control device is diagrammed schematically in FIG. 1 of U.S. Pat. No. 5,270,622. The brushless electric motor comprises a stator, a rotor unit with a magnetic element and a sensor system for detecting the alignment of the magnetic element. The signals of the sensor system are sent to the control device, which delivers drive signals to the motor as a function of the rotational speed, as specified by the user, and as a function of the sensor signals. The sensor system is usually designed as part of the stator and is fixedly connected thereto, usually by a casting compound. The sensor system for detecting the alignment of the magnetic element and the brushless electric motor are arranged at a separate location spaced from the control device and are connected by lines for relaying the signals.

The disadvantage of such an embodiment lies in its complex design, which necessitates several steps during assembly, in particular mounting the sensor system on the stator, installing the control device in the handle and connecting the sensor system to the control device via multiple lines.

For hygienic reasons, such medical handles must be sterilized after being used, so it is necessary to protect the electric and electronic components from aggressive ambient conditions that prevail during sterilization. This is usually accomplished by casting the components in resin and/or encapsulating them in hermetically sealed housings. The points of admission of lines and cables into the cast material or the housing constitute weaknesses where leakage may occur and subsequently water vapor or corrosive media such as cleaning agents can penetrate to the electric and electronic components and damage them, resulting in premature failure of the handle and necessitating complex repair measures or complete replacement of the device, which is a disadvantage.

Finally, there is repeatedly the problem that while connecting the sensor system to the electric motor by casting with resin the insulation of the signal line between the sensor system and the control device may melt, so that satisfactory functioning of the handle is impaired. This also necessitates additional testing work after assembly to ensure that the lines are intact and/or repairs on or replacement of the lines are necessary if the lines have been damaged.

One object is therefore to create a medical handle that will not have the aforementioned disadvantages. The handle should be easy to assemble in particular and should be more resistant to the ambient conditions that prevail during sterilization than is the case with known handles.

SUMMARY

According to one embodiment of the medical handle the sensor system for detecting or determining the alignment, i.e., the angle of rotation, of the at least one magnetic element (motor sensor system) and the control and/or regulating circuit are combined in a common control module. Combining the motor sensor system and the control and/or regulating circuit into a one-piece component simplifies assembly and greatly facilitates installation in the handle in particular. To allow these parts to be combined into a one-piece control module and be used in the medical handle, it is also necessary to modify the design of the handle and to arrange the sensor system, the control and/or regulating circuit and, optionally, additional components installed in the control module, accordingly. Additional components installed in the control module may include in particular at least parts of the circuit for selecting the drive rotational speed and/or at least parts of the circuit for selecting the direction of rotation of the brushless electric motor and/or electric contacts to an energy source and/or contacts for connecting the control module, in particular the control and/or regulating circuit, to the drive unit and/or at least parts of a circuit for temperature monitoring of heat-emitting components of the handle, e.g., batteries and/or at least parts of a circuit for voltage monitoring of voltage-carrying components of the handle, e.g., for low-voltage shutdown of batteries.

The design of the handle can be modified in that the at least one magnetic element whose position or alignment is determined by the sensors is arranged in the medical handle in such a way that at least a part of the control module can be positioned in the immediate vicinity of the at least one magnetic element. The magnetic element may be formed by either the rotor magnet itself or by a separate sensor magnet rotating with the rotor magnet in a known way.

In a first embodiment, the medical handle is equipped with a grip section and a function section arranged at an angle thereto, comprising, for example, the tool receptacle, an illumination device, media lines and other function elements, wherein the at least one magnetic element is arranged in one of the two sections and the control module is accommodated at least partially in the section in which the at least one magnetic element is not situated. The brushless motor is preferably also accommodated in the function section, wherein the at least one magnetic element is arranged in an area of the function section, where the grip section is connected so that the control module is accommodated at least partially in the grip section. One advantage of this embodiment is that at least parts of circuits that cooperate with control members that may be arranged on or attached to the grip section may be integrated into the control module in such a way that preferably all circuits are combined in a single compact control module. These additional circuits may be, for example, a circuit for selecting the drive rotational speed or a circuit for selecting the direction of rotation of the brushless electric motor. Another advantage of this embodiment is the excellent utilization of the available space in the interior of the handle, in particular when the control module has an elongated narrow preferably essentially square shape, so that it can be installed with no problem in the grip section of the handle.

In a second embodiment, the medical handle has a tool receptacle for the medical tool or a connecting device for a tool receptacle, and the rotor unit is equipped with a rotor and a sensor magnet, wherein the sensor magnet and the control module are arranged between the rotor and the tool receptacle and/or the connecting device. This handle is preferably an elongated essentially tubular element having a first end with the tool receptacle and a second opposite end. Such a handle, in contrast with the handle of the first embodiment, does not have a separate grip section in which the control module can be accommodated at least partially. With these elongated handles, for technical assembly reasons the sensor magnet is usually arranged at the second end, i.e., between the rotor and the end of the instrument. If, as proposed according to one embodiment, the sensor system for detecting the alignment of the at least one magnetic element and the control and/or regulating circuit are combined in one common control module, then there remains too little space in this end area of the handle, where the sensor magnet is situated, to additionally accommodate the control module there. Only through the arrangement of the sensor magnet between the rotor and the tool receptacle and/or the connecting device there is created enough room for the control module to be able to position the control module in the immediate vicinity of the sensor magnet.

The sensor system for detecting the alignment of the at least one magnetic element must be arranged in the control module in such a way that it can be positioned in the immediate vicinity of the at least one magnetic element. If the control module is designed with an elongated shape, e.g., essentially a square, straight or curved shape, so that it has a first end and a second end, then it is advantageous to accommodate the sensor system directly at one of the two ends of the control module, the end with the sensor system being arranged in the immediate vicinity of the at least one magnetic element when the control module is installed in the medical handle. If necessitated by the space conditions in the interior of the handle, the control module may also be designed in an angular shape, e.g., T-shaped or L-shaped, and may also have two or more arms connected to one another and more than two ends. Again with these embodiments, it is advantageous to arrange the sensor system directly at one of these ends and to arrange the end with the sensor system again in the immediate vicinity of the at least one magnetic element. Alternatively, the control module may be essentially U-shaped, with the sensor system being provided, for example, on the outside of the crossbar which connects the two legs of the U-shaped control module, which are of equal or different lengths, so that the sensor system is situated at the approximate center of the control module. The crossbar is arranged in the immediate vicinity of the at least one magnetic element. In this way, it is possible in particular in the case of elongated handles to position the sensor system in the immediate vicinity of the at least one magnetic element, while all the other circuits are distributed over the elongated interior of the handle. The embodiments of the control module and the arrangement of the sensor system presented here are of course intended only as examples, which those skilled in the art can easily modify accordingly, adapting them to the prevailing spatial conditions in the interior of the handle.

In one additional embodiment, to further improve on the determination of the alignment of the at least one magnetic element by the sensor system, the control module is provided with a defined exterior shape, so that the arrangement of the control module in the immediate vicinity to be at least one magnet is additionally facilitated and promoted. In particular the control module comprises an accommodation for at least partially accommodating or surrounding the at least one magnetic element. The control module preferably has a setback in the form of an arc of a circle or a step or it has a bore for at least partially accommodating the at least one magnetic element. The sensor system is especially preferably mounted immediately adjacent to the setback or the bore.

To facilitate handling and to simplify installation in the handle, the control module preferably has a carrier device, in particular a carrier plate or a circuit board to which at least the control and/or regulating circuit and the sensor system are attached, especially preferably also at least parts of other circuits.

Alternatively or additionally, the control module may also be at least partially accommodated in a housing, the housing preferably being designed so that the components in the interior of the housing are not impaired in their function due to the ambient conditions prevailing during a cleaning or sterilization process. In addition to the control and/or regulating circuit and the sensor system, these components may also include the abovementioned parts of the circuit for selecting the drive speed or for selecting the rotational direction, electric contacts to an energy source, contacts for connecting the control module, in particular the control and/or regulating circuit to the drive unit, the carrier device or cooling elements for dissipating the heat generated during operation of the control module.

The requirements about conditions the housing must withstand during a cleaning and sterilization process are known, so they need not be discussed in detail here. In particular, depending on the type of sterilization or cleaning, the housing must be designed so that it can withstand temperatures of at least 120° C., pressure fluctuations of approximately 3 bar or a chemically aggressive and corrosive environment for at least 10 minutes. For example, the housing may be made of suitable heat-resistant plastics, resins or metals and can have a hermetically sealed interior, so that water vapor or cleaning agents can also be prevented from penetrating into the interior even after repeated cleaning or sterilization. A housing is also understood to include embedding the control module in a cast material, e.g., a synthetic resin, in particular epoxy or silicone resins.

Another advantage of combining the sensor system and the control and/or regulating circuit in a joint control module consists of simple alignment of the sensor system with the at least one magnetic element, e.g., a sensor magnet. The exact alignment of the sensor system is extremely important for the operating performance of the drive unit, in particular for the precise control and power supply to the brushless electric motor. The precise arrangement of the sensor system with respect to the at least one magnetic element is achieved by a precise defined distance of the sensor system from at least one other component provided in the control module. Contacts which connect the control module to other components in the handle and/or by means of which the control module can be connected to other components are preferably used for this, especially preferably the contacts that connect the control module to the drive unit. These contacts may be designed as plug contacts, for example, so that by installing the control module in the handle, in particular by plugging the contacts together, not only the connection of the control module to the drive unit is accomplished, but at the same time the arrangement and accurate alignment of the sensor system with respect to the at least one magnetic element are also achieved.

The invention is explained in greater detail below on the basis of preferred embodiments with reference to the accompanying drawings, in which:

DETAILED DESCRIPTION

Figure 1:
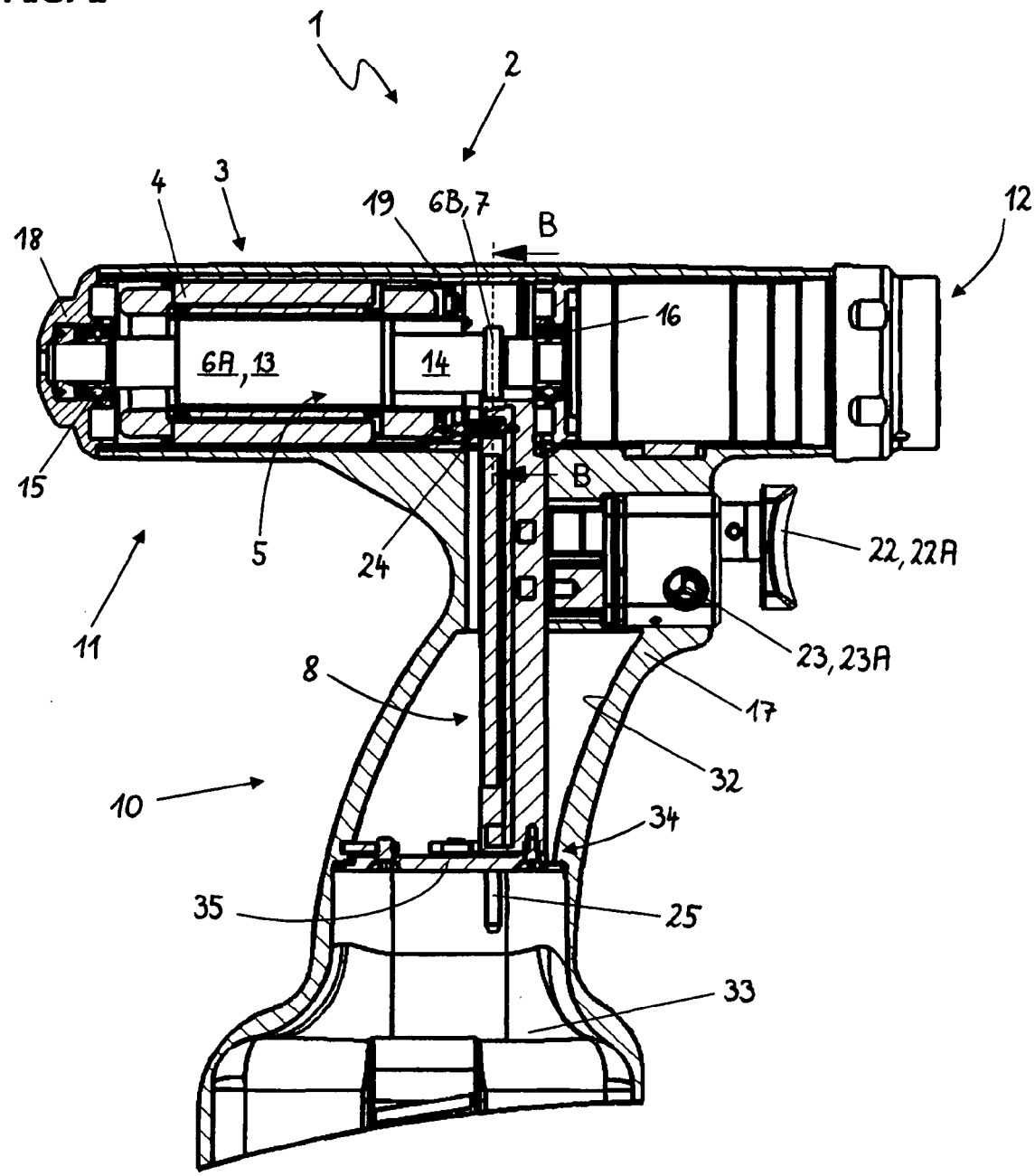
FIG. 1 shows a cross-section of a preferred embodiment of a handle in elevation.

The handle 1 shown in FIG. 1 is designed as a pistol shaped instrument comprising one or more outer sleeves 17, a function section 11 and a grip section 10 arranged at an angle to the former. However, the present invention is not limited to this shape of the handle but instead it may also be applied equally to other types of handles. The drive unit 2, comprising at least one brushless electric motor 3 with a stator 4 and a rotor unit 5, and the tool receptacle or a connection device 12 for connecting the handle 1 to a tool receptacle are both accommodated in the function section 11. A sealing cap 18, which seals the function section 11 and accommodates or supports on shoulders and setbacks components arranged in the interior of the handle 1, is provided on the end of the tubular or sleeve-shaped function section 11, which is opposite the end with the tool receptacle or the connecting device 12.

In a known way, both the drive unit 2 and the function section 11 may also contain other components, e.g., gears, devices for converting the rotational movement of the electric motor 3 into another type of movement, e.g., into an oscillating, circular or reciprocating movement, lighting devices with light sources and/or optical fibers, media lines, e.g., for liquids or gases, memory units for storing data, e.g., operating data, sensors, e.g., for tool recognition, etc. The tool receptacle or the connecting device 12 for connecting the handle 1 to a tool receptacle are preferably designed to be detachable, so that a wide variety of tools, e.g., rotary drills, saw blades, shavers, reamers, files, etc., can also be connected to the handle 1.

Since brushless electric motors are known, the design of the motor 3 will be discussed further below only inasmuch as is necessary for an understanding of the invention. The electric motor 3 is accommodated in a motor bushing 19. The rotor unit 5 consists of the rotor 13, at least one magnetic element and a rotor shaft 14. The rotor 13 may therefore be arranged around the rotor shaft 14 and mounted on it or it may itself form the rotor shaft 14 or be designed as part of the rotor shaft 14. The rotor shaft 14 is mounted in one or more bearings, preferably ball bearings 15, 16. The rotor 13 is magnetic or is provided with magnets, so that it forms a first magnetic element 6A. A second magnetic element 6B is designed as a sensor magnet 7 and is mounted on the rotor shaft 14 at a distance from the rotor 13. The sensor magnet 7 rotates with the rotor 13 and is used in a known way for determining the alignment, i.e., the angle of rotation of the first magnetic element 6A, so that the electric motor 3 has accurate control and power supply.

The grip section 10 has an ergonomic outer shape so that even lengthy holding of the handle 1 by the user does not cause rapid fatigue of the hand and arm. A first actuator element 22 with a first displaceable push button 22A is arranged on the grip section 10. By means of this button, the user is able to control the rotational speed of the electric motor 3. By means of a second actuator element 23 with a shift pin 23A that is displaceable across the push button 22A, the user is able to adjust the direction of rotation of the electric motor 3. Push button 22A and shift pin 23A are accommodated partially in handle 1 through openings in the outer sleeve 17. Push button 22A and shift pin 23A are each assigned circuits that are arranged in the handle 1 for generating a shift signal or a control signal.

The grip section 10 is designed to be hollow over most of its length so that various components and/or accessories of the handle 1 are fixedly accommodated and detachably inserted in this cavity 32, in particular one or more batteries or accumulators 33 to supply power to the handle 1. The batteries or accumulators 33 are connected by electric lines or contacts to all the electric consumers in the handle 1. To seal off the hollow space 32 and to secure the batteries 33, the grip section 10 has a closure device on its free end, e.g., a closing cap. As an alternative, the power supply to the handle 1 may also be provided via an external energy source outside of the handle 1, in particular via a connection to an electric power supply network.

A control module 8 is also accommodated at least partially in the hollow space 32 of the grip section 10; this control module combines at least the sensor system 9 (FIGS. 2-4) for determining the alignment, i.e., the angle of rotation of the sensor magnet 7 and of the rotor 13 as well as the control and/or regulating circuit for controlling and/or regulating the drive unit 2. The control and/or regulating circuit generates in a known manner a drive signal for driving the electric motor 3. It receives measurement signals from the sensor system 9 regarding one or more drive parameters of the electric motor 3, in particular its rotational speed, then compares these measured signals with a preselected value and varies the drive signal as a function of the deviation between the measurement signal and the preselected value. The sensor system 9 may comprise any of the known sensors for detecting the strength of a magnetic field, in particular Hall sensors 37 or reed contacts.

The control module 8 is mounted in the handle by means of one or more fastening devices. A first fastening device 34 comprises a separating plate 35 which is provided between the batteries 33 and the control module 8 and is connected by one or more screws to the handle 1 and the control module 8. Several openings are provided in the separation plate 35 through which the power supply lines or contact elements 25 connecting the electric consumers in the handle 1 to the batteries 33 run. The contact elements 24 which connect the control module 8 to the drive unit 2 and by which the drive signals in particular are sent to the electric motor 3 may serve as a second fastening device for the control module 8, wherein the contacts 24 are preferably designed as plug contacts.

Figure 4:
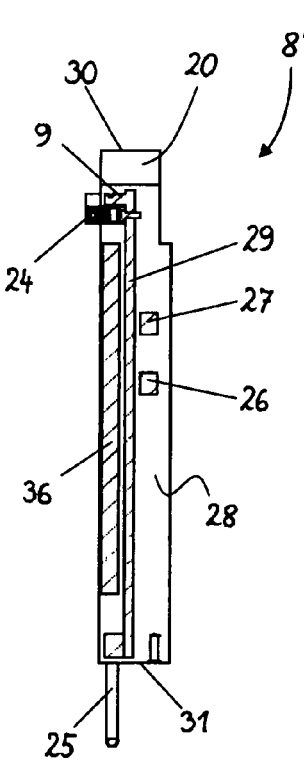
FIG. 4 shows a longitudinal section through an embodiment of the control module.

FIG. 4 shows a preferred embodiment of a control module. This control module 8' is designed to be elongated, essentially in the form of a cuboid, having a first end 30 and a second end 31 and also including several additional components in addition to the sensor system 9 for determining the alignment of the at least one magnetic element 6A, 6B and of the rotor 13 and the control and/or regulating circuit for controlling and/or regulating the drive unit 2: reference numeral 26 refers to a part of the circuit by means of which the direction of rotation of the electric motor 3 can be changed. The circuit 26 preferably comprises a sensor for determining the strength of a magnetic field, but it may of course also be composed of other sensors if other signal generators are used. For switching from running clockwise to counterclockwise or vice versa, the user shifts the shift pin 23A and the magnet connected to it from a first position into a second position in which the shift pin 23A remains. The sensor for determining the strength of the magnetic field, in particular a reed contact or a Hall sensor is arranged so it is offset in relation to the shift pin 23A and the magnet, so that the magnetic field strength changes as a result of its displacement. The Hall sensor sends a measurement signal as a function of the measured magnetic field strength to the circuit 26, which subsequently selects the proper direction of rotation of the electric motor 3.

Reference numeral 27 is assigned to a part of the circuit which allows the user to preselect the rotational speed for the electric motor 3. The circuit 27 preferably comprises a sensor for determining the strength of the magnetic field, in particular a reed contact or a Hall sensor but it may of course also be comprised of other sensors when other signal generators are used. Actuator member 22 is connected to a magnet whose distance from the sensor can be varied by displacement of the pushbutton 22A in relation to the sensor. The sensor and the circuit 27 in turn determine the magnetic field strength and generate a corresponding signal, which is relayed to the control and/or regulating circuit for controlling and/or regulating the drive unit 2 and serves as a preselected value for the rotational speed.

The circuits 26, 27, the sensor system 9 and the control and/or regulating circuit for controlling and/or regulating the drive unit 2 are arranged on a shared carrier device in the form of a circuit board 29. In addition, the contact elements 24 which connect the control module 8 to the drive unit 2 and the contact elements 25 which are connected to the power source for the handle 1, in particular the batteries 33, are part of the control module 8'. The contact elements 24, 25 may be designed as flat contacts, spring contacts or preferably as plug contacts, for example.

Control module 8' additionally comprises a heat sink 36, which may consist of one or more cooling plates, for example. Heat sink 36 is made of a material having a high thermal conductivity, in particular metal. It dissipates the heat generated by the electric and electronic components of the control module 8' and delivers at least a portion of this heat to the environment.

According to the embodiment in FIG. 4, the circuit boards 29, the sensor system 9, the control and/or regulating circuit for controlling and/or regulating the drive unit 2, at least the parts of the circuits 26, 27 which are attached to the circuit board 29, the heat sink 36 and at least parts of the contacts 24, 25 are all accommodated in a housing 28. The housing 28 is preferably made of plastic, especially preferably a cast material. The housing 28 is preferably hermetically sealed so that all the components arranged in its interior are sealed from the environment so that they are not impaired in their function by the ambient conditions prevailing during a cleaning or sterilization process. Manufacturing the housing 28 from a cast material in particular has the advantage that essentially no air inclusions or large cavities filled with air are present in the control module 8' so there is a better dissipation of heat out of the control module 8'. The housing 28 may also serve as a carrier device, so that no separate carrier device such as that described above is required.

Combining the circuits mentioned above, the sensor system 9, the contact elements 24, 25 and optionally other circuits, e.g., a circuit for monitoring temperature or a circuit for monitoring the voltage in a single control module 8, 8' and encapsulation of same in a housing 28 has the advantage in particular that the connecting lines between the individual circuits are also completely enclosed. It is thus no longer necessary to insulate the connecting lines, so there is no danger of destroying this insulation in casting the housing and this eliminates the points of admission of the lines to the individual circuits which, as described above, are especially susceptible to develop leaks and allow moisture or cleaning agents to penetrate as far as the circuits. Instead of a large number of connections and contacts between the individual circuits and sensors arranged at different locations in the handle, all of which must be sealed and insulated, there are thus only two interfaces with the control device combined in the single control module 8, 8', namely the connection to the drive unit 2 via the contact elements 24 and the connection to the energy source via the contact elements 25.

The control module 8, 8' thus has two major advantages: due to its compactness, it facilitates in particular installation in the handle 1 and thus allows rapid and easy replaceability in repairs. If the control module 8, 8' is additionally provided with a housing 28 that is hermetically sealed and protects the components of the control module 8, 8' during a cleaning or sterilization process, then this creates a handle 1 whose control device withstands frequent sterilization or cleaning without being impaired and without the user having to perform any additional measures before or after sterilization or cleaning.

To allow the parts to be combined in a one-piece control module 8, 8' and to allow the latter to be installed in the medical handle 1, it is necessary, among other things, to modify the design of the handle 1. In particular, at least one of the two magnets 6A, 6B must be arranged in the handle 1 in such a way that at least a part of the control module 8, 8' can be positioned in the immediate vicinity of the at least one magnetic element 6A, 6B. This is achieved in the embodiment according to FIG. 1 by the fact that the sensor magnet 7 is arranged in an area of the function section 11 where the grip section 10 is connected. If a part of the control module 8, 8', e.g., the first end 30 is now applied to the sensor magnet 7 in the function section 11, then each part of the control module 8, 8' which does not find any room in the function section 11 can be positioned in the hollow space 32 of the grip section 10.

Figure 2:
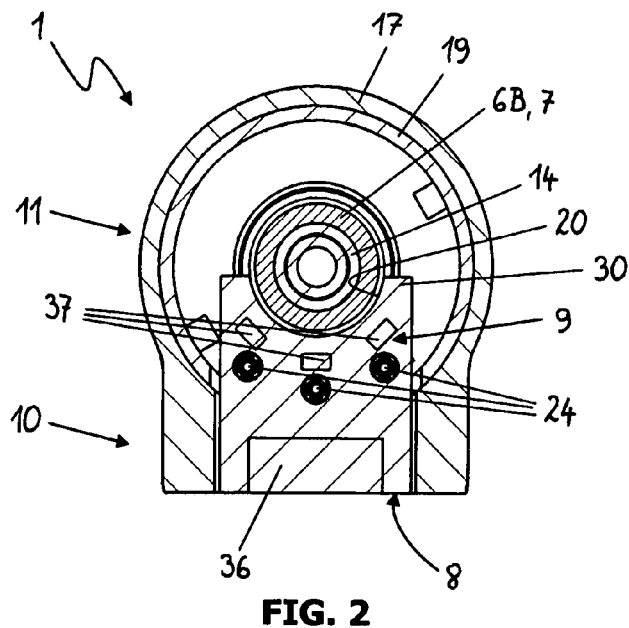
FIG. 2 shows a sectional diagram along line B-B in FIG. 1 through the function section, the magnetic element and a part of the control module.

FIG. 2 shows a sectional diagram through the handle 1 according to FIG. 1 along line B-B, which shows clearly the arrangement of the control module 8 in the immediate vicinity of the sensor magnet 7 and to the part in the function section 11 and that in the grip section 10. In the embodiments according to FIGS. 1, 2 and 4, the sensor system 9 is arranged at the outermost end 30 of the control module 8, 8' so that it can be positioned in the immediate vicinity of the sensor magnet 7. In these figures, the first end 30 of the control module 8, 8' is additionally designed by shaping a circular setback 20 in such a way that it facilitates the arrangement of the sensor magnet 7 and the sensor system 9 in immediate vicinity of one another. The sensor system 9 preferably comprises three Hall sensors 37 which are arranged at approximately 45° or 60° intervals around the arch-shaped setback 20 and the sensor magnet 7.

Figure 3:
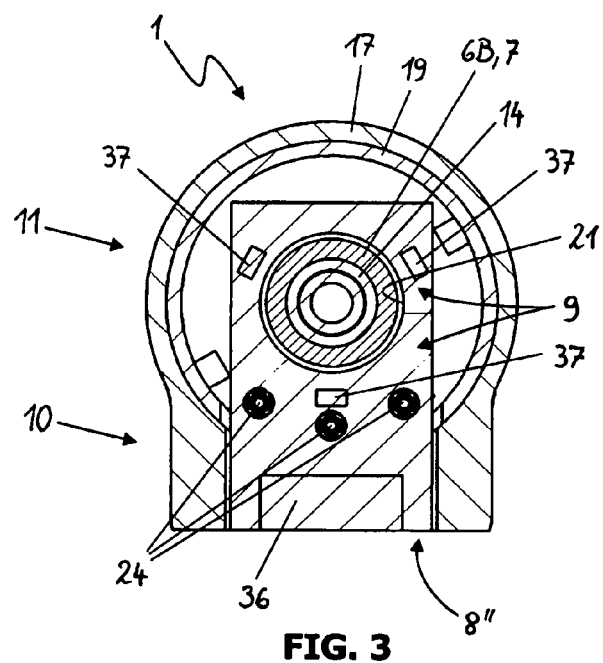
FIG. 3 is similar to FIG. 2, but shows an alternative embodiment of the control module.

FIG. 3 shows another embodiment of the control module 8". Control module 8" comprises a bore 21, in which the sensor magnet 7 is accommodated. The advantage of this embodiment is that the manufacturer has the option of positioning several Hall sensors 37 around the sensor magnet 7 or varying the distances between the Hall sensors 37, e.g., arranging the sensors 37 with intervals of 120° from one another. It is thus possible to achieve a more accurate determination of the alignment of the magnetic element 6A, 6B.

With regard to the exact alignment of the Hall sensors 37 with respect to the sensor magnet 7, the contacts 24 are preferably used. The contacts 24 and the Hall sensors 37 are attached to the circuit board 29 at a fixed distance from one another. The circuit board 29 is assembled with the electronic and electric components with an extremely high precision, so that the spatial distances between different components are highly constant. This precise spatial arrangement of the components and the constant distance between the components are used for the alignment of the Hall sensors 37 with respect to the sensor magnet 7 in that the control module 8 is mounted in the handle 1 via the contacts 24 while at the same time achieving the result that the Hall sensors 37 are aligned with the magnetic element 6A, 6B with sufficient accuracy and without additional assembly complexity.

As can be seen from FIGS. 2 and 3 the sensor system 9 for determining the alignment of the at least one magnetic element 6A, 6B comprises at least two, preferably three or more, Hall sensors 37, which surround the at least one magnetic element 6A, 6B in an arch-shaped or circular configuration. Due to this configuration the sensors 37 are arranged closer to the magnetic element 6A, 6B, which leads to an improved and more accurate determination of the alignment of the at least one magnetic element 6A, 6B.

The present invention is not limited to the embodiment described here, but instead comprises all possible embodiments which do not alter the basic proper function principle of the invention. In particular, the drive unit 2 may also be designed as an electric motor without a sensor magnet and the position of the rotor may be determined directly via the magnetic rotor or rotor equipped with magnets. In this embodiment the control module 8 is to be arranged in the immediate vicinity of the rotor and/or to the rotor magnet.

What is claimed is:

1. A medical handle comprising
a grip section, a function section, a drive unit adapted to drive a medical tool and a control and/or regulating circuit adapted to control and/or regulate the drive unit, wherein the drive unit comprises a brushless electric motor with a stator, a rotor unit including a rotor and at least one magnetic element that rotates with the rotor and a sensor system for determining the alignment of the at least one magnetic element by determining an angle of rotation of the at least one magnetic element, the sensor system sensing the at least one magnetic element that rotates with the rotor and the rotational movement of the motor, wherein the sensor system for determining the alignment of the at least one magnetic element and the control and/or regulating circuit are combined in a one-piece joint control module, wherein the at least one magnetic element is arranged in the medical handle in such a way that at least a part of the control module can be positioned in the immediate vicinity of the at least one magnetic element and wherein the sensor system for determining the alignment of the at least one magnetic element is arranged in the control module in such a way that it can be positioned in the immediate vicinity of the at least one magnetic element,
wherein the control module has an elongated shape that is accommodated partially in the grip section and the function section and comprises a first end turned toward the drive unit and a second end turned toward an energy source for supplying energy to the handle,
wherein the first end is provided with contact elements which connect the control module to the drive unit for the supply of drive signals to the drive unit and the second end is provided with electrical contact elements for connecting the control module to the energy source,
wherein the medical handle has a tool receptacle for the medical tool or a connecting device for a tool receptacle, and wherein the rotor unit comprises the rotor and one of the at least one magnetic element which is in the form of a sensor magnet, and wherein the sensor magnet and the control module are arranged between the rotor and the tool receptacle of the connecting device, and wherein the sensor system comprises at least two sensors positioned to surround the at least one magnetic element in an arch-shaped or circular configuration.

2. The medical handle according to claim 1, wherein the control module is shaped in such a way that the at least one magnetic element and the sensor system for determining the alignment of the at least one magnetic element can be arranged in direct proximity to one another.

3. The medical handle according to claim 2, wherein the control module comprises an accommodation for at least partially accommodating or surrounding the at least one magnetic element.

4. The medical handle according to claim 3, wherein the accommodation comprises one of an arch-shaped setback, a step-shaped setback or a bore.

5. The medical handle according to claim 1, wherein the sensor system for determining the alignment of the at least one magnetic element is arranged on one of the first end and the second ends of the control module.

6. The medical handle according to claim 1, wherein the function section is arranged at an angle to the grip section, wherein the at least one magnetic element is arranged in one of the two sections.

7. The medical handle according to claim 6, wherein the at least one magnetic element is arranged in an area of the function section to which the grip section is adjacent, and the control module is accommodated at least partially in the grip section.

8. The medical handle according to claim 1, wherein the control module comprises a carrier device that is one of a carrier plate or a circuit board on which at least the control and/or regulating circuit and the sensor system are mounted.

9. The medical handle according to claim 1, wherein the control module is surrounded at least partially by a housing.

10. The medical handle according to claim 9, wherein the housing is designed so that the operability of the components in the interior of the housing can be maintained even after frequent cleaning or sterilization.

11. The medical handle according to claim 9, wherein the housing comprises a hermetically sealed interior.

12. The medical handle according to claim 9, wherein the housing comprises a cast material, which embeds the control module.

13. The medical handle according to claim 1, wherein the control module further comprises at least one of the following:

at least parts of the circuit for selecting the drive rotational speed, at least parts of the circuit for selecting the direction of rotation of the electric motor, at least parts of a circuit for monitoring the temperature of heat-emitting components of the handle, and at least parts of a circuit for monitoring the voltage of voltage-carrying parts of the handle.

14. The medical handle according to claim 1, wherein the control module comprises:

an elongate body having the first end and the second end;

a housing substantially surrounding and hermetically sealing the elongate body, and the electrical contact elements positioned on the elongate body adjacent the second end, the electrical contact elements having a portion that extends through the housing and is removably connectable to a source of electric power.

15. The medical handle of claim 14, wherein the contact elements positioned on the first end of the elongate body have a portion that projects through the housing, the portion of the contact elements being connectable to provide electric power to the motor.

16. The medical handle of claim 14, wherein the first end of the elongate body is shaped to allow the sensor system to be positioned in operative relationship with the at least one magnetic element.

17. The medical handle of claim 14, wherein the medical handle has a pistol-grip shaped body with a grip section and a function section arranged at an angle to the grip section, the control module being configured for positioning inside the pistol-shaped body with the first end projecting into the function section and a remainder of the control module extending into the grip section.

18. The medical handle of claim 14, wherein the control module comprises one or more additional sensors mounted on the elongate body and within the housing, the one or more sensors being operable to sense magnetic elements of a variable user control used to selectively change an operation of the electric motor.

19. The medical handle according to claim 14, wherein the housing is designed so that the operability of the components in the interior of the housing can be maintained even after frequent cleaning or sterilization.

20. The medical handle according to claim 14, wherein the housing comprises a cast material within which the control module is embedded.

* * * * *